US009855537B2

(12) United States Patent
Williams

(10) Patent No.: US 9,855,537 B2
(45) Date of Patent: Jan. 2, 2018

(54) IMPELLER ASSEMBLIES FOR FLUID PROCESSING SYSTEMS

(71) Applicant: LIFE TECHNOLOGIES CORPORATION, Carlsbad, CA (US)

(72) Inventor: Trevor G. Williams, Providence, UT (US)

(73) Assignee: Life Technologies Corporation, Carlsbad, CA (US)

( * ) Notice: Subject to any disclaimer, the term of this patent is extended or adjusted under 35 U.S.C. 154(b) by 364 days.

(21) Appl. No.: 14/660,405

(22) Filed: Mar. 17, 2015

(65) Prior Publication Data

US 2015/0265988 A1    Sep. 24, 2015

Related U.S. Application Data

(60) Provisional application No. 61/969,094, filed on Mar. 22, 2014.

(51) Int. Cl.
*B01F 7/00* (2006.01)
*B01F 15/00* (2006.01)

(52) U.S. Cl.
CPC ........ *B01F 15/00681* (2013.01); *B01F 7/001* (2013.01); *B01F 7/00675* (2013.01); *B01F 7/00691* (2013.01); *B01F 15/0085* (2013.01); *B01F 2215/0073* (2013.01)

(58) Field of Classification Search
CPC ... B01F 7/001; B01F 7/00675; B01F 7/00691
USPC ................................................ 366/308, 331
See application file for complete search history.

(56) References Cited

U.S. PATENT DOCUMENTS

| 3,322,401 | A | 5/1967 | Mersch |
| 3,559,962 | A | 2/1971 | Enssle et al. |
| 3,692,427 | A | 9/1972 | Risse |
| 4,083,653 | A | 4/1978 | Stiffler |
| 4,722,608 | A | 2/1988 | Salzman et al. |
| 5,885,001 | A | 3/1999 | Thomas |
| 5,941,636 | A | 8/1999 | Lu |
| 6,083,587 | A | 7/2000 | Smith et al. |
| 6,670,171 | B2 | 12/2003 | Carll |
| 7,384,783 | B2 | 6/2008 | Kunas et al. |

(Continued)

FOREIGN PATENT DOCUMENTS

| DE | 202009005407 U1 | 9/2009 |
| DE | 102008058338 A1 | 5/2010 |

(Continued)

OTHER PUBLICATIONS

International Search Report and Written Opinion dated Jun. 26, 2015, issued in PCT Application No. PCT/US2015/021037, filed Mar. 17, 2015.

*Primary Examiner* — David Sorkin
(74) *Attorney, Agent, or Firm* — Workman Nydegger

(57) ABSTRACT

A fluid mixing system includes a flexible bag having an interior surface bounding a compartment. An elongated first tubular connector is disposed within the compartment of the flexible bag, the first tubular connector having a first end and an opposing second end, the first end of the first tubular connector being coupled with the flexible bag. An elongated second tubular connector is disposed within the compartment of the flexible bag, the second tubular connector being more rigid than the first tubular connector and having a first end coupled to the second end of the first tubular connector. A plurality of impeller are disposed on the elongated second tubular connector at spaced apart locations.

20 Claims, 12 Drawing Sheets

(56) References Cited

U.S. PATENT DOCUMENTS

| | | |
|---|---|---|
| 7,441,940 B2 | 10/2008 | Vanek |
| 7,487,688 B2 | 2/2009 | Goodwin |
| 7,682,067 B2 | 3/2010 | West et al. |
| 7,878,099 B2 | 2/2011 | Loibl |
| 7,879,599 B2 | 2/2011 | Goodwin et al. |
| 8,455,242 B2 | 6/2013 | Staheli et al. |
| 8,506,198 B2 | 8/2013 | West et al. |
| 8,603,805 B2 | 12/2013 | Goodwin et al. |
| 8,641,314 B2 | 2/2014 | Thacker et al. |
| 2002/0105856 A1 | 8/2002 | Terentiev |
| 2002/0131654 A1 | 9/2002 | Smith et al. |
| 2003/0077466 A1 | 4/2003 | Smith et al. |
| 2006/0240546 A1 | 10/2006 | Goodwin et al. |
| 2006/0270036 A1 | 11/2006 | Goodwin et al. |
| 2006/0280028 A1 | 12/2006 | West et al. |
| 2010/0260010 A1* | 10/2010 | Jornitz ................ B01F 7/0005 366/343 |
| 2011/0026360 A1 | 2/2011 | Greller et al. |
| 2011/0188928 A1 | 8/2011 | West et al. |
| 2011/0229963 A1 | 9/2011 | Fatherazi et al. |
| 2011/0310696 A1 | 12/2011 | Goodwin et al. |
| 2013/0101982 A1 | 4/2013 | Goodwin et al. |
| 2014/0106453 A1 | 4/2014 | Kunas et al. |
| 2015/0117142 A1* | 4/2015 | Staheli ................ B01F 7/00058 366/331 |

FOREIGN PATENT DOCUMENTS

| | | |
|---|---|---|
| FR | 782935 | 9/1934 |
| JP | H06285353 A | 10/1994 |
| WO | 2011/139209 A1 | 11/2011 |
| WO | 2013/151733 A1 | 10/2013 |

* cited by examiner

IMPELLER ASSEMBLIES FOR FLUID PROCESSING SYSTEMS

CROSS-REFERENCE TO RELATED APPLICATIONS

This application claims priority to U.S. Provisional Patent Application No. 61/969,094 filed Mar. 22, 2014, which is incorporated herein by specific reference.

BACKGROUND OF THE INVENTION

1. The Field of the Invention

The present invention relates to impeller assemblies used with fluid processing systems such as bioreactors and fermentors.

2. The Relevant Technology

The biopharmaceutical industry uses a broad range of mixing systems for a variety of processes such as in the preparation of media and buffers and in the growing, mixing and suspension of cells and microorganisms. Some conventional mixing systems, including bioreactors and fermentors, comprise a flexible bag disposed within a rigid support housing. An impeller is disposed within the flexible bag and is coupled with a drive shaft projecting into the bag. Rotation of the drive shaft and impeller facilitates mixing and/or suspension of the fluid contained within flexible bag.

Although the current mixing systems are useful, they have some limitations. For example, where the drive shaft is secured within the flexible bag during the manufacturing process, the rigid drive shaft limits the ability to collapse or fold the flexible bag so as to reduce its size for transportation, storage and/or further processing. Likewise, where it is intended to reuse the drive shaft, such as when it is made of metal, this system has the disadvantage of needing to clean and sterilize the drive shaft between different uses.

In an alternative mixing system, a flexible tube is disposed within a flexible bag. A first end of the tube is rotatably coupled by a dynamic seal to the bag while an opposing second end of the tube is sealed to an impeller. During use, a rigid drive shaft is passed down into the tube and couples with the impeller. In turn, rotation of the drive shaft facilitates rotation of the tube and impeller for mixing the fluid within the flexible bag. In this design, before the drive shaft is inserted, the combined flexible bag and tube can be folded for ease of storage and transportation. In addition, the tube isolates the drive shaft from the fluid so that during use the drive shaft does not directly contact the fluid within the bag. As such, following use, the drive shaft can be removed and reused without the need for cleaning or sterilization.

Although the mixing system using the flexible tube has a number of improved advantages, it also has some limitations. For example, the flexible tube design is limited to a single impeller mounted on the end thereof. In larger volume mixing systems or in applications where higher rates of mixing are required, a single impeller may not be sufficient to achieve a needed mixing rate. Accordingly, what is needed in the art are mixing systems that retain all or some of the advantages of using the flexible tube to isolate the rigid drive shaft from the fluid but enable higher mixing rates relative to the single impeller design.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
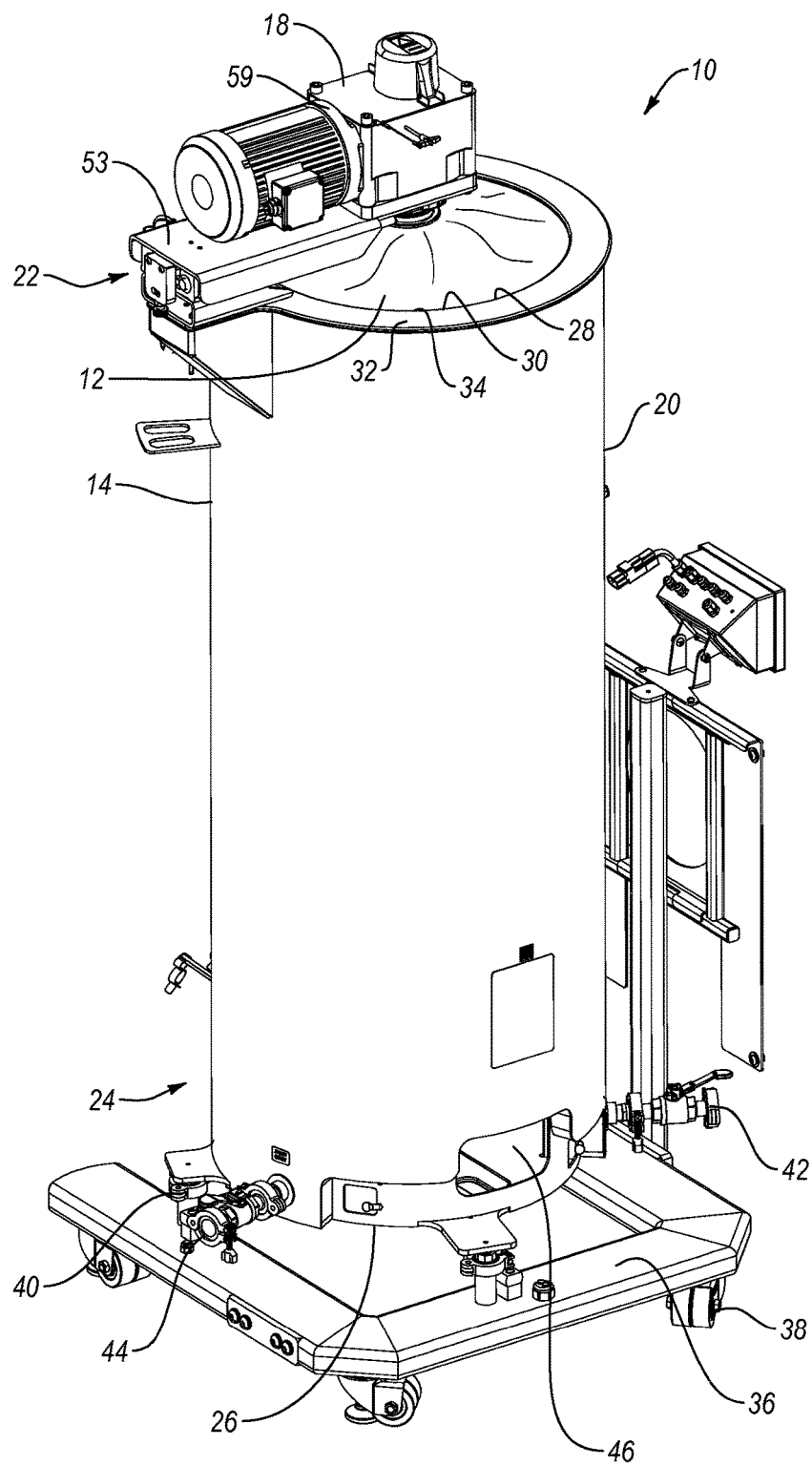
FIG. 1 is a perspective view of a fluid mixing system.

Before describing the present disclosure in detail, it is to be understood that this disclosure is not limited to particularly exemplified apparatus, systems, methods, or process parameters that may, of course, vary. It is also to be understood that the terminology used herein is only for the purpose of describing particular embodiments of the present disclosure, and is not intended to limit the scope of the invention.

All publications, patents, and patent applications cited herein, whether supra or infra, are hereby incorporated by reference in their entirety to the same extent as if each individual publication, patent, or patent application was specifically and individually indicated to be incorporated by reference.

The term "comprising" which is synonymous with "including," "containing," "having" or "characterized by," is inclusive or open-ended and does not exclude additional, unrecited elements or method steps.

It will be noted that, as used in this specification and the appended claims, the singular forms "a," "an" and "the" include plural referents unless the content clearly dictates otherwise. Thus, for example, reference to a "port" includes one, two, or more ports.

As used in the specification and appended claims, directional terms, such as "top," "bottom," "left," "right," "up," "down," "upper," "lower," "inner," "outer," "internal," "external," "interior," "exterior," "proximal," "distal" and the like are used herein solely to indicate relative directions and are not otherwise intended to limit the scope of the invention or claims.

Where possible, like numbering of elements have been used in various figures. Furthermore, alternative configurations of a particular element may each include separate letters appended to the element number. Accordingly, an appended letter can be used to designate an alternative design, structure, function, implementation, and/or embodiment of an element or feature without an appended letter. For instance, an element "80" may be embodied in an alternative configuration and designated "80a." Similarly, multiple instances of an element and or sub-elements of a parent element may each include separate letters appended to the element number. In each case, the element label may be used without an appended letter to generally refer to instances of the element or any one of the alternative elements. Element labels including an appended letter can be used to refer to a specific instance of the element or to distinguish or draw attention to multiple uses of the element.

Various aspects of the present devices, systems, and methods may be illustrated with reference to one or more exemplary embodiments. As used herein, the term "embodiment" means "serving as an example, instance, or illustration," and should not necessarily be construed as preferred or advantageous over other embodiments disclosed herein.

Various aspects of the present devices and systems may be illustrated by describing components that are coupled, attached, and/or joined together. As used herein, the terms "coupled", "attached", "connected" and/or "joined" are used to indicate either a direct connection between two components or, where appropriate, an indirect connection to one another through intervening or intermediate components. In contrast, when a component is referred to as being "directly coupled", "directly attached", "directly connected" and/or "directly joined" to another component, there are no intervening elements present.

Unless defined otherwise, all technical and scientific terms used herein have the same meaning as commonly understood by one of ordinary skill in the art to which the present disclosure pertains. Although a number of methods and materials similar or equivalent to those described herein can be used in the practice of the present disclosure, the preferred materials and methods are described herein.

The present invention relates to fluid processing systems and related methods for mixing and sparging solutions and/or suspensions. The processing systems can be bioreactors or fermentors used for culturing cells or microorganisms. By way of example and not by limitation, the inventive systems can be used in culturing bacteria, fungi, algae, plant cells, animal cells, protozoans, nematodes, and the like. The systems can accommodate cells and microorganisms that are aerobic or anaerobic and are adherent or non-adherent. The systems can also be used in association with the formation and/or treatment of solutions and/or suspensions that are not biological but nevertheless incorporate mixing. For example, the systems can be used in the production of media, chemicals, food products, beverages, and other liquid products.

The inventive systems are designed so that a majority of the system components that contact the material being processed can be disposed of after each use. As a result, the inventive systems substantially eliminate the burden of cleaning and sterilization required by conventional stainless steel mixing and processing systems. This feature also ensures that sterility can be consistently maintained during repeated processing of multiple batches. In view of the foregoing, and the fact that the inventive systems are easily scalable, relatively low cost, and easily operated, the inventive systems can be used in a variety of industrial and research facilities that previously outsourced such processing.

Depicted in FIG. 1 is one embodiment of an inventive fluid processing system 10 incorporating features of the present invention. In general, processing system 10 comprises a container 12 that is disposed within a rigid support housing 14. A mixer system 18 is designed for mixing and/or suspending components within container 12. The various components of fluid processing system 10 will now be discussed in greater detail.

With continued reference to FIG. 1, support housing 14 has a substantially cylindrical sidewall 20 that extends between an upper end 22 and an opposing lower end 24. Lower end 24 has a floor 26 mounted thereto. Support housing 14 has an interior surface 28 that bounds a chamber 30. An annular lip 32 is formed at upper end 22 and bounds an opening 34 to chamber 30. Floor 26 of support housing 14 rests on a cart 36 having wheels 38. Support housing 14 is removable secured to cart 36 by connectors 40. Cart 36 enables selective movement and positioning of support housing 14. In alternative embodiments, however, support housing 14 need not rest on cart 36 but can rest directly on a floor or other structure.

Although support housing 14 is shown as having a substantially cylindrical configuration, in alternative embodiments support housing 14 can have any desired shape capable of at least partially bounding a compartment. For example, sidewall 20 need not be cylindrical but can have a variety of other transverse, cross sectional configurations such as polygonal, elliptical, or irregular. Furthermore, it is appreciated that support housing 14 can be scaled to any desired size. For example, it is envisioned that support housing 14 can be sized so that chamber 30 can hold a volume of less than 50 liters or more than 1,000 liters. Support housing 14 is typically made of metal, such as stainless steel, but can also be made of other materials capable of withstanding the applied loads of the present invention.

In one embodiment of the present invention means are provided for regulating the temperature of the fluid that is contained within container 12 disposed within support housing 14. By way of example and not by limitation, electrical heating elements can be mounted on or within support housing 14. The heat from the heating elements is transferred either directly or indirectly to container 12. Alternatively, in the depicted embodiment support housing 14 is jacketed with one or more fluid channels being formed therein. The fluid channels have a fluid inlet 42 and a fluid outlet 44 that enables a fluid, such as water or propylene glycol, to be pumped through the fluid channels. By heating, cooling or otherwise controlling the temperature of the fluid that is passed through the fluid channels, the temperature of support housing 14 can be regulated which in turn regulates the temperature of the fluid within container 12 when container 12 is disposed within support housing 14. Other conventional means can also be used such as by applying gas burners to support housing 14 or pumping the fluid out of container 12, heating or cooling the fluid and then pumping the fluid back into container 12. When using container 12 as part of a bioreactor or fermentor, the means for heating can be used to heat the culture within container 12 to a temperature in a range between about 30° C. to about 40° C. Other temperatures can also be used.

Support housing 14 can have one or more opening 46 formed on the lower end of sidewall 20 and on floor 26 to enable gas and fluid lines to couple with container 12 and to enable various probes and sensors to couple with container 12 when container 12 is within support housing 14. Further disclosure on support housing 14 and alternative designs thereof is disclosed in U.S. Pat. No. 7,682,067 and US Patent Publication No. 2011-0310696, which are incorporated herein by specific reference.

Figure 2:
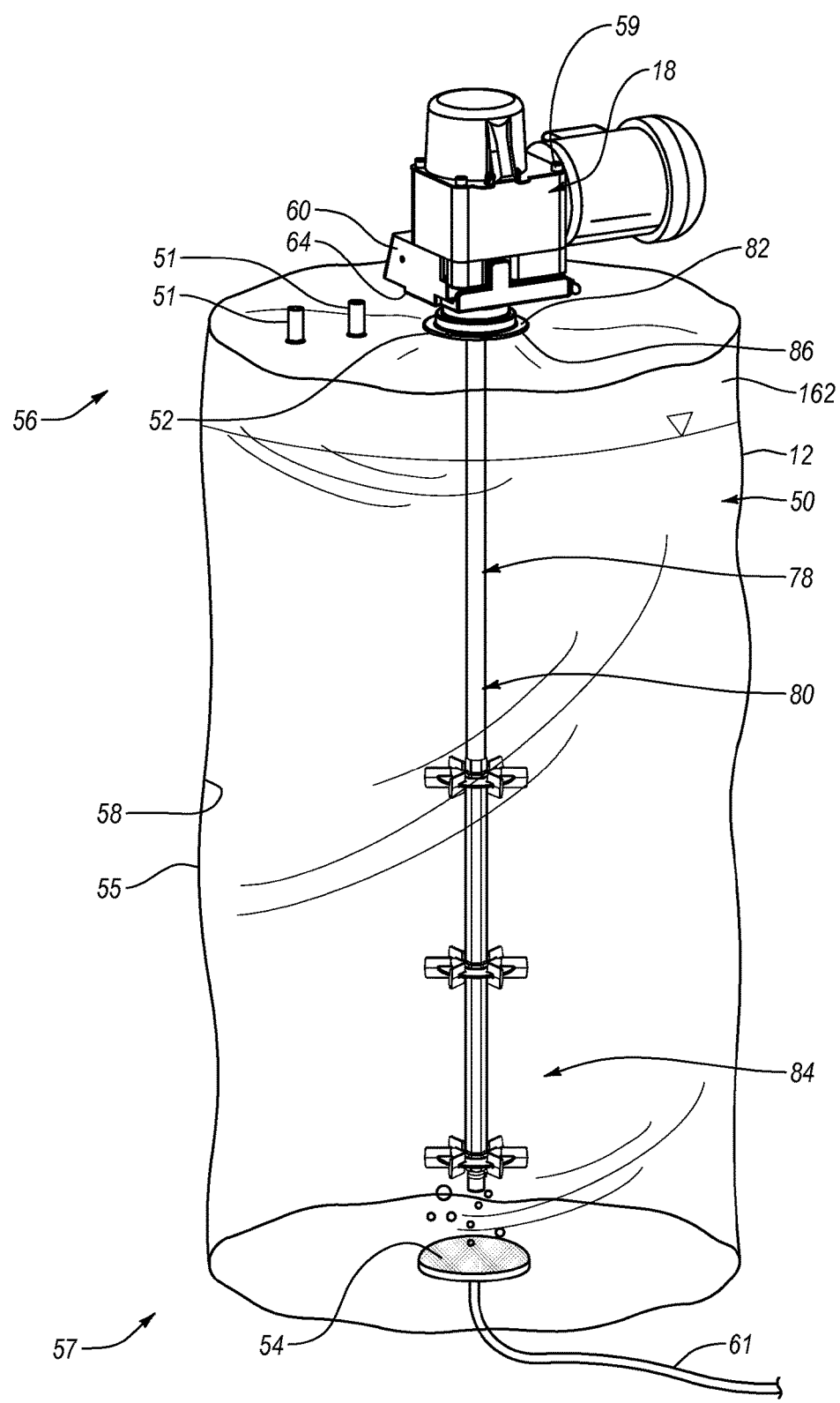
FIG. 2 is a perspective view of the container assembly and drive motor assembly of the fluid mixing system shown in FIG. 1.

FIG. 2 shows container 12 coupled with mixer system 18. Container 12 has a side 55 that extends from an upper end 56 to an opposing lower end 57. Container 12 also has an interior surface 58 that bounds a compartment 50 in which a portion of mixer system 18 is disposed. In the embodiment depicted, container 12 comprises a flexible bag. Formed on container 12 are a plurality of ports 51 that communicate with compartment 50. Although only two ports 51 are shown, it is appreciated that container 12 can be formed with any desired number of ports 51 and that ports 51 can be formed at any desired location on container 12 such as upper end 56, lower end 57, and/or alongside 55. Ports 51 can be the same configuration or different configurations and can be used for a variety of different purposes. For example, ports 51 can be coupled with fluid lines for delivering media, cell cultures, and/or other components into and out of container 12.

Ports 51 can also be used for coupling probes to container 12. For example, when container 12 is used as a bioreactor for growing cells or microorganisms, ports 51 can be used for coupling probes such as temperatures probes, pH probes, dissolved oxygen probes, and the like. Examples of ports 51 and how various probes and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference. Ports 51 can also be used for coupling container 12 to secondary containers and to other desired fittings.

In one embodiment of the present invention, means are provided for delivering a gas into the lower end of container 12. By way of example and not by limitation, as also depicted in FIG. 2, a sparger 54 can be either positioned on or mounted to lower end 57 of container 12 for delivering a gas to the fluid within container 12. As is understood by those skilled in the art, various gases are typically required in the growth of cells or microorganisms within container 12. The gas typically comprises air that is selectively combined with oxygen, carbon dioxide and/or nitrogen. However, other gases can also be used. The addition of these gases can be used to regulate the dissolved oxygen and $CO_2$ content and to regulate the pH of a culture solution. Depending on the application, sparging with gas can also have other applications. A gas line 61 is coupled with sparger 54 for delivering the desired gas to sparger 54. Gas line 61 need not pass through lower end 57 of container 12 but can extend down from upper end 56 or from other locations.

Sparger 54 can have a variety of different configurations. For example, sparger 54 can comprise a permeable membrane or a fitted structure comprised of metal, plastic or other materials that dispense the gas in small bubbles into container 12. Smaller bubbles can permit better absorption of the gas into the fluid. In other embodiments, sparger 54 can simply comprise a tube, port, or other type opening formed on or coupled with container 12 through which gas is passed into container 12. In contrast to being disposed on container 12, the sparger can also be formed on or coupled with mixer system 18. Examples of spargers and how they can be used in the present invention are disclosed in United States Patent Publication Nos. 2006-0270036 and 2006-0240546 which were previously incorporated by reference. Other conventional spargers can also be used. It is appreciated that in some embodiments and uses that a sparger may not be required.

In the depicted embodiment, container 12 has an opening 52 that is sealed to a rotational assembly 82 of mixer system 18, which will be discussed below in greater detail. As a result, compartment 50 is sealed closed so that it can be sterilized and be used in processing sterile fluids. During use, container 12 is disposed within chamber 30 of support housing 14 as depicted in FIG. 1. Container 12 is supported by support housing 14 during use and can subsequently be disposed of following use. In one embodiment, container 12 comprised of a flexible, water impermeable material such as a low-density polyethylene or other polymeric sheets or film having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet that comprises two or more layers of different materials that can be separated by a contact layer. All of the layers are simultaneously co-extruded. One example of an extruded material that can be used in the present invention is the Thermo Scientific CX3-9 film available from Thermo Fisher Scientific. The Thermo Scientific CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the Thermo Scientific CX5-14 cast film also available from Thermo Fisher Scientific. The Thermo Scientific CX5-14 cast film comprises a polyester elastomer outer layer, an ultra-low density polyethylene contact layer, and an EVOH barrier layer disposed therebetween.

The material is approved for direct contact with living cells and is capable of maintaining a solution sterile. In such an embodiment, the material can also be sterilizable such as by radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003, which are hereby incorporated by specific reference.

In one embodiment, container 12 comprise a two-dimensional pillow style bag wherein two sheets of material are placed in overlapping relation and the two sheets are bounded together at their peripheries to form the internal compartment. Alternatively, a single sheet of material can be folded over and seamed around the periphery to form the internal compartment. In another embodiment, the containers can be formed from a continuous tubular extrusion of polymeric material that is cut to length and is seamed closed at the ends.

In still other embodiments, container 12 can comprise a three-dimensional bag that not only has an annular side wall but also a two dimensional top end wall and a two dimensional bottom end wall. Three dimensional containers comprise a plurality of discrete panels, typically three or more, and more commonly four or six. Each panel is substantially identical and comprises a portion of the side wall, top end wall, and bottom end wall of the container. Corresponding perimeter edges of each panel are seamed together. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1, published Sep. 19, 2002, which is hereby incorporated by reference.

It is appreciated that container 12 can be manufactured to have virtually any desired size, shape, and configuration. For example, container 12 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes. The size of the compartment can also be in the range between any two of the above volumes. Although container 12 can be any shape, in one embodiment container 12 is specifically configured to be complementary or substantially complementary to chamber 30 of support housing 14. It is desirable that when container 12 is received within chamber 30, container 12 is at least generally uniformly supported by support housing 14. Having at least general uniform support of container 12 by support housing 14 helps to preclude failure of container 12 by hydraulic forces applied to container 12 when filled with fluid.

Although in the above discussed embodiment container 12 has a flexible, bag-like configuration, in alternative embodiments it is appreciated that container 12 can comprise any form of collapsible container or semi-rigid container. Container 12 can also be transparent or opaque and can have ultraviolet light inhibitors incorporated therein.

Mixer system 18 is used for mixing and/or suspending a culture or other solution or suspension within container 12. As depicted in FIG. 2, mixer system 18 generally comprises a drive motor assembly 59 that is mounted on support housing 14 (FIG. 1), an impeller assembly 78 coupled to and projecting into container 12, and a drive shaft 72 (FIG. 4) that extends between drive motor assembly 59 and impeller assembly 78.

Figure 3:
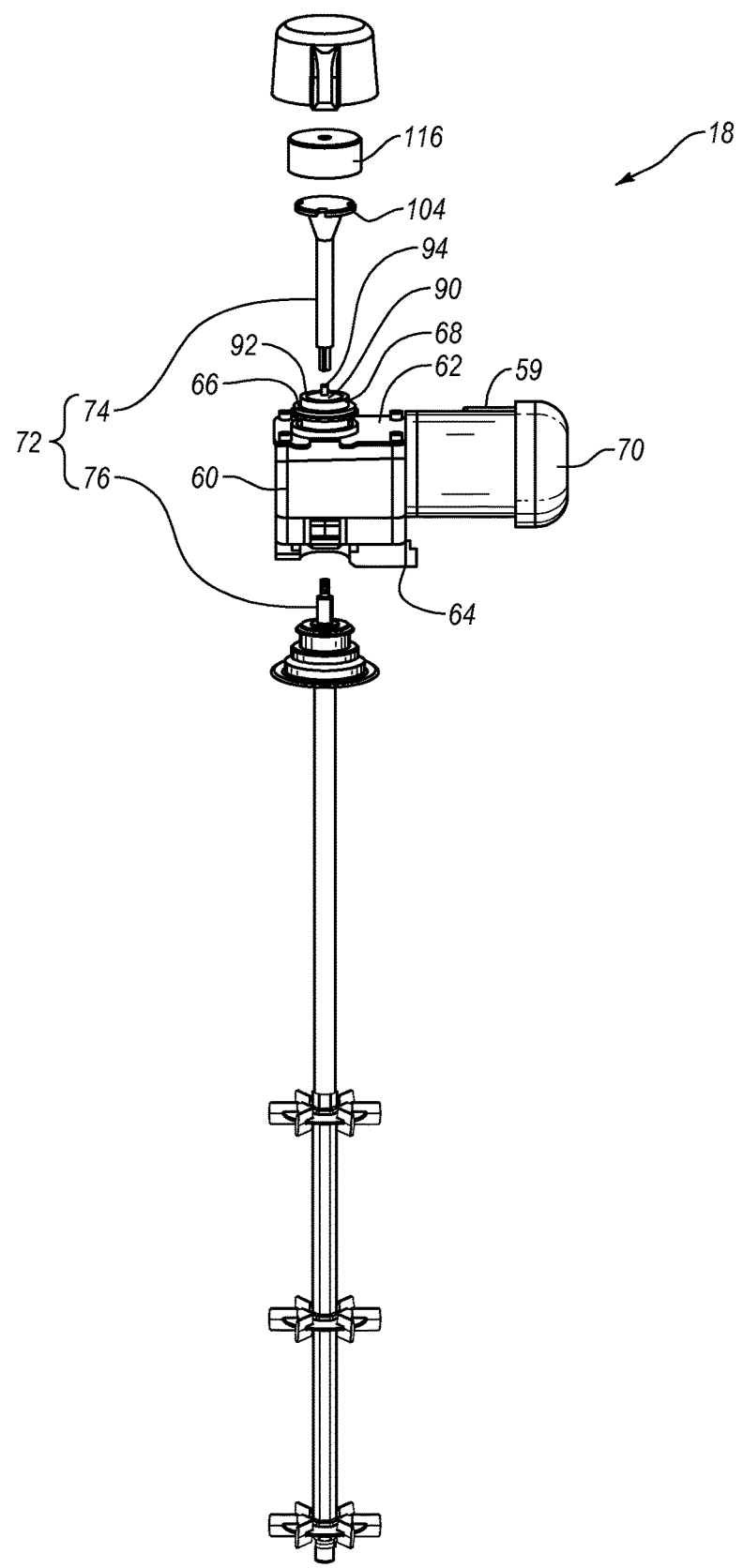
FIG. 3 is a perspective view of the impeller assembly, drive shaft and drive motor shown in FIG. 2.
Figure 4:
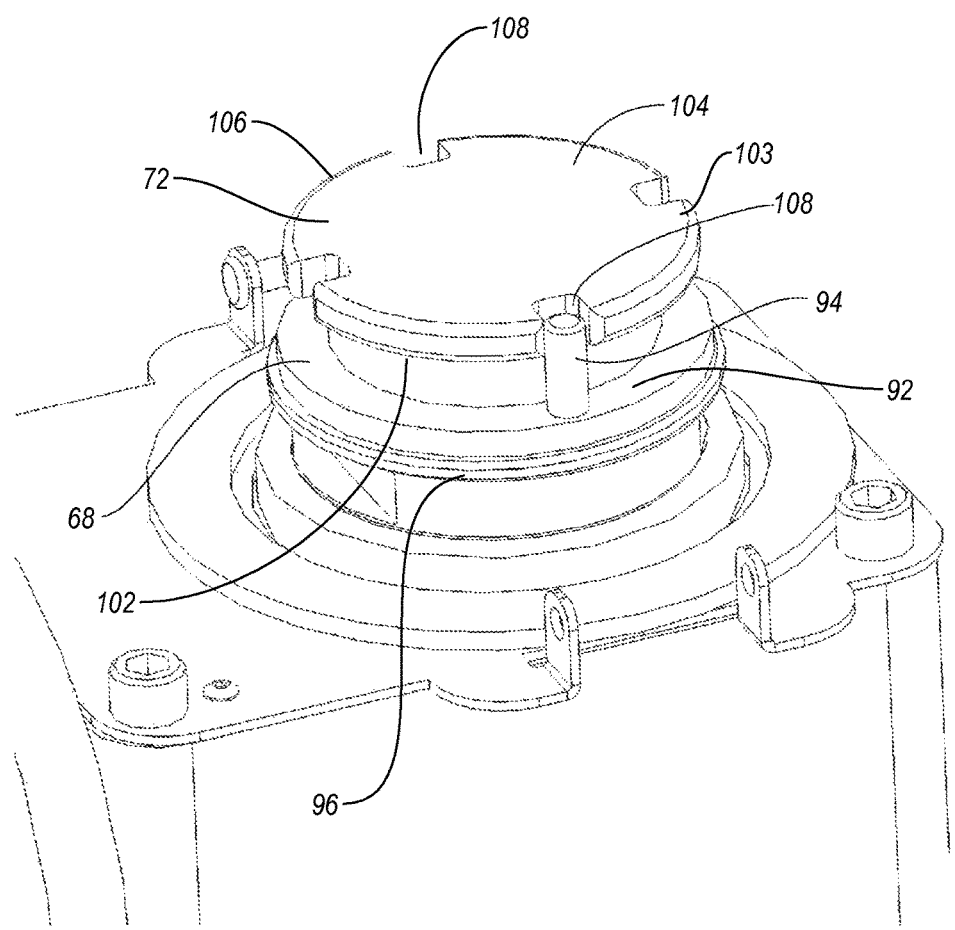
FIG. 4 is a perspective view of the drive shaft in FIG. 3 being coupled with the drive motor assembly.

Turning to FIG. 3, drive motor assembly 59 comprises a housing 60 having a top surface 62 and an opposing bottom surface 64 with an opening 66 extending through housing 60 between surfaces 62 and 64. A tubular motor mount 68 is rotatably secured within opening 66 of housing 60 and bounds a passage 90 extending therethrough. As depicted in FIG. 4, the upper end of motor mount 68 terminates at an ends face 92 having a locking pin 94 outwardly projecting therefrom. A thread 96 encircles motor mount 68 adjacent to end face 92. Returning to FIG. 3, a drive motor 70 is mounted to housing 60 and engages with motor mount 68 so as to facilitate select rotation of motor mount 68 relative to housing 60. As depicted in FIG. 1, drive motor assembly 59 is coupled with support housing 14 by a bracket 53. In alternative embodiments, however, drive motor assembly 59 can be mounted on a separate structure adjacent to support housing 14.

Figure 5:
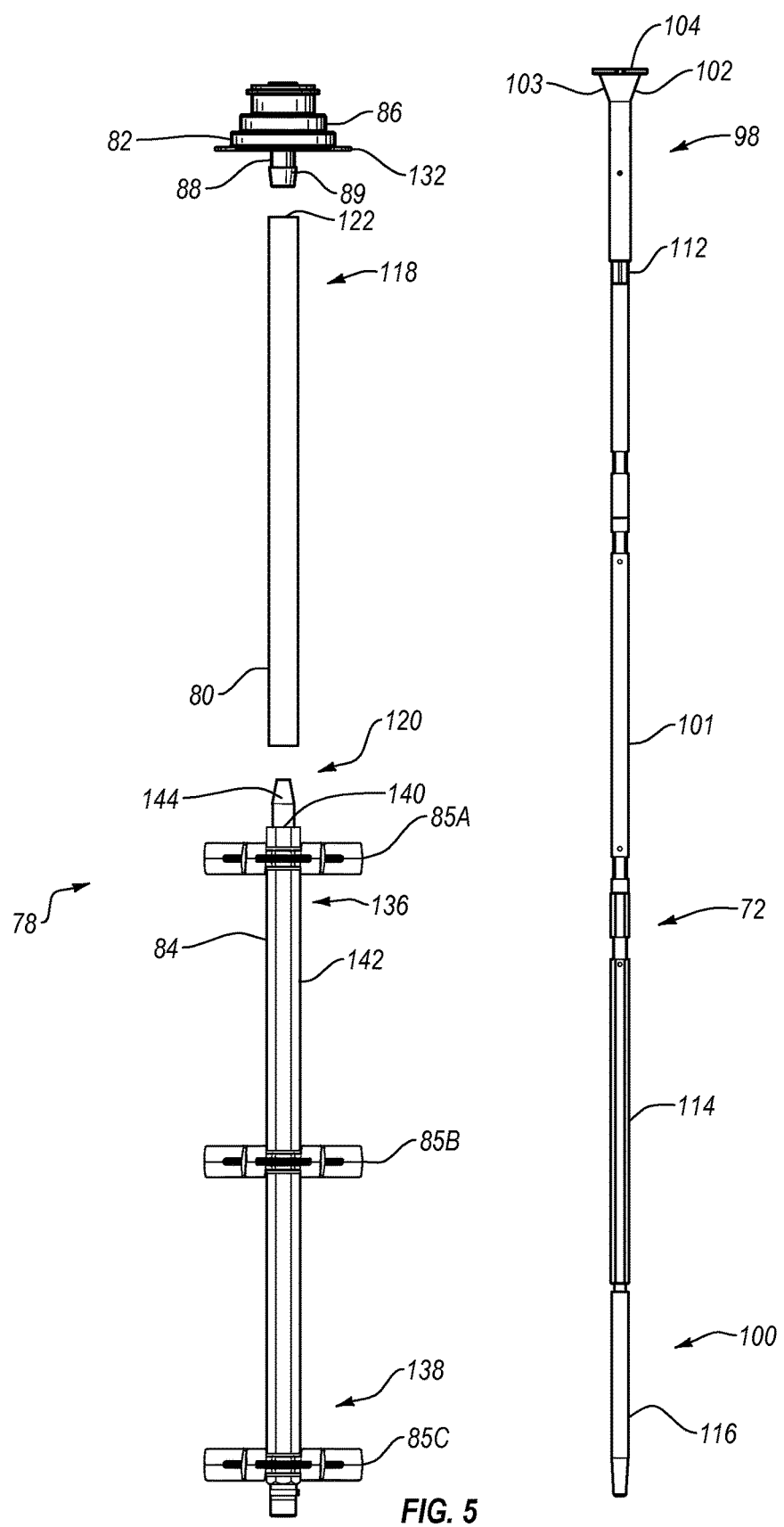
FIG. 5 is an elevated side view of the impeller assembly and drive shaft shown in FIG. 3.

Drive shaft 72 is configured to pass through motor mount 68 and thus through housing 60. Turning to FIG. 5, drive shaft 72 has a first end 98 and an opposing second end 100 and generally comprises a shaft portion 101 with a head 103 mounted on the end thereof. Head 103 includes a substantially frustoconical engaging portion 102 that is complimentary to an engaging portion formed within the upper end of motor mount 68. As a result, the two engaging portions can be complementary mated to facilitate contacting engagement between motor mount 68 and drive shaft 72 when drive shaft 72 is passed through motor mount 68.

As depicted in FIG. 4, head 103 also includes a substantially circular plate 104 disposed on top of engaging portion 102. Plate 104 extends to a perimeter edge 106 that radially outwardly projects beyond engaging portion 102. A plurality of spaced apart notches 108 are formed on perimeter edge 106. When drive shaft 72 is passed through motor mount 68, plate 104 rests on or slightly above end face 92 of motor mount 68 so that locking pin 94 is received within a notch 108. As a result, drive shaft 72 is locked to motor mount 68 so that rotation of motor mount 68 facilitates concurrent rotation of drive shaft 72. A cap 116 (FIG. 3) can be threaded onto the end of motor mount 70 to prevent drive shaft 72 from disengaging from motor mount 70.

Returning to FIG. 5, shaft portion 101 comprises a first driver portion 112 and a second driver portion 114. Driver portions 112 and 114, as will be discussed below in greater detail, typically have a polygonal transverse cross section. For example, driver portions 112 and 114 can have 5, 6, 7, or more sides. In other embodiments, the transverse cross of section of driver portions 112 and 114 can be other non-circular shapes such as oval or irregular. The remainder of shaft portion 101 typically has a circular transverse cross section with a maximum diameter that is smaller than the maximum diameter of driver portions 112 and 114. Second end 116 of drive shaft 72 terminates at a nose 116 that is inwardly tapered for easy insertion.

In one embodiment drive shaft 72 can comprise a single, unitary shaft. In other embodiments, draft shaft 72 can be comprised of multiple sections that are selectively threaded or otherwise secured together. For example, drive shaft can comprise a head section 74 and a separate shaft section 76 that can be coupled together as depicted in FIG. 3. Drive shaft 72 can be formed from 2, 3, 4, 5 or more sections that are selectively coupled together. Drive shaft 72 can be comprised of high strength polymers, ceramics, composites, metals, such as aluminum, stainless steel, or other metal alloys, or other materials. Furthermore, different sections can be made of different materials.

By forming drive shaft 72 from multiple sections, it is easy to form a shaft having a desired length by adding or removing sections. Furthermore, the modular drive shaft 72 can be used in a room with a low ceiling height. For example, a first section of drive shaft 72 can be partially advanced down through motor mount 68. Additional sections can then be progressively attached thereto as the sections are progressively advanced down through motor mount 68. Accordingly, the full length of drive shaft 72 need not be simultaneously raised above motor mount 68 for passing therethrough. Alternative embodiments of drive shafts that can be used in the present inventive system, including examples of how separate sections can be coupled together, are disclosed in U.S. Pat. No. 8,641,314 which issued on Feb. 4, 2014 and which is incorporated herein by specific reference.

As depicted in FIG. 5, impeller assembly 78 comprises an elongated first tubular connector 80 having rotational assembly 82 secured at one end and an elongated second tubular connector 84 coupled at the opposing end. A plurality of impellers 85A-C are disposed along the length of second tubular connector 84. More specifically, first tubular connector 80 has a first end 118 and an opposing second end 120 with an interior surface that bounds a passage 122 that extends along the length thereof. In one embodiment first tubular connector 80 comprises a flexible tube that can typically be bent along its length over and angle of 90° and more commonly 180° or 270° without plastic deformation. Tubular connector 80 is typically made from, comprises or consists of a sufficiently flexible material, such as an elastomeric material, so that tubular connector can withstand repeated bending and deformation without appreciable structural yield and can possess a durometer on the Shore OO scale that is typically less than 98 and often less than 60 or 30. Other values can also be used. First tubular connector 80 can be formed from a polymeric material such flexible PVC or other polymers having the desired properties.

Figure 6:
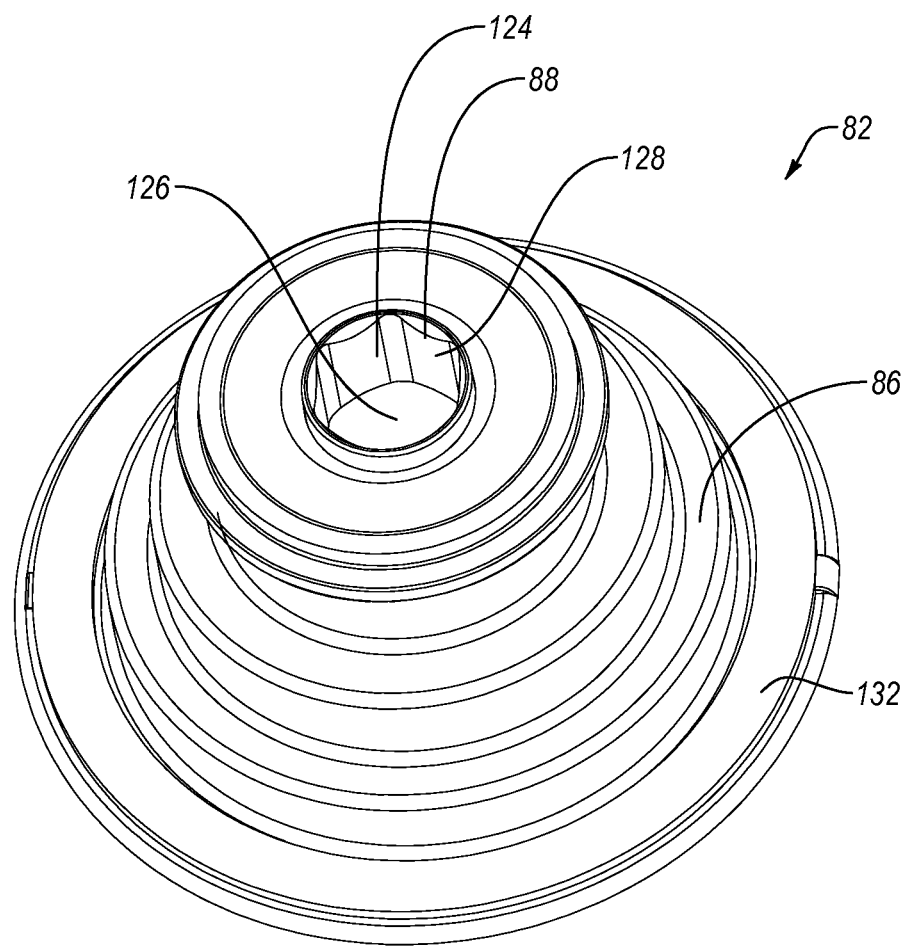
FIG. 6 is an enlarged top perspective view of the rotational assembly shown in FIG. 5.

Rotational assembly 82 comprises an outer casing 86 and a tubular hub 88 that centrally extends through outer casing 86 and is rotatably coupled thereto. One or more dynamic seals can be formed between outer casing 86 and tubular hub 88 so that a sterile seal can be maintained therebetween. Furthermore, one or more bearings can be positioned between outer casing 86 and tubular hub 88 to enable easy rotation of hub 88 relative to casing 86. As depicted in FIG. 6, hub 88 has an interior surface 124 that bound a passage 126 extending therethrough. At least a section of interior surface 124 forms an engaging portion 128 that is complementary to the transverse cross section of first driver portion 112 on drive shaft 72 (FIG. 5) or is otherwise configured to engage first driver portion 112 so that when first driver portion 112 is received within engaging portion 128, rotation of drive shaft 72 facilitates rotation of hub 88 relative to casing 86.

Returning to FIG. 5, hub 88 includes a barbed stem 89 that downwardly projects below casing 86. Stem 89 is configured to be received within first end 118 of first tubular connector 80 so that a liquid tight seal is formed therebetween and so that stem 89 is secured to first tubular connector 80. Casing 86 includes an annular, outwardly projecting flange 132 which, as depicted in FIG. 2, is welded or otherwise secured to container 12 so as to secure casing to container 12 within opening 52 thereof. In this configuration, first tubular connector 80 projects into compartment 50 of container 12.

Returning to FIG. 5, second tubular connector 84 has a first end 136 and an opposing second end 138 with an interior surface 140 and an exterior surface 142 extending therebetween. Interior surface 140 bounds a passage 141 (FIG. 11) extending therethrough. In one embodiment, second tubular connector 84 is more rigid than first tubular connector 80. For example, in different embodiments second tubular connector 84 cannot be bent along its length over and angle of 20°, 40°, 90° or 120° without plastic deformation. Tubular connector 84 is typically not made from and does not comprise or consists of an elastomeric material. Rather, tubular connector 84 is typically comprised of a rigid plastic or other material so that tubular connector 84 has a durometer on the Shore D scale that is typically greater than 20 and often greater than 40 or 60. Other values can also be used.

Figure 7:
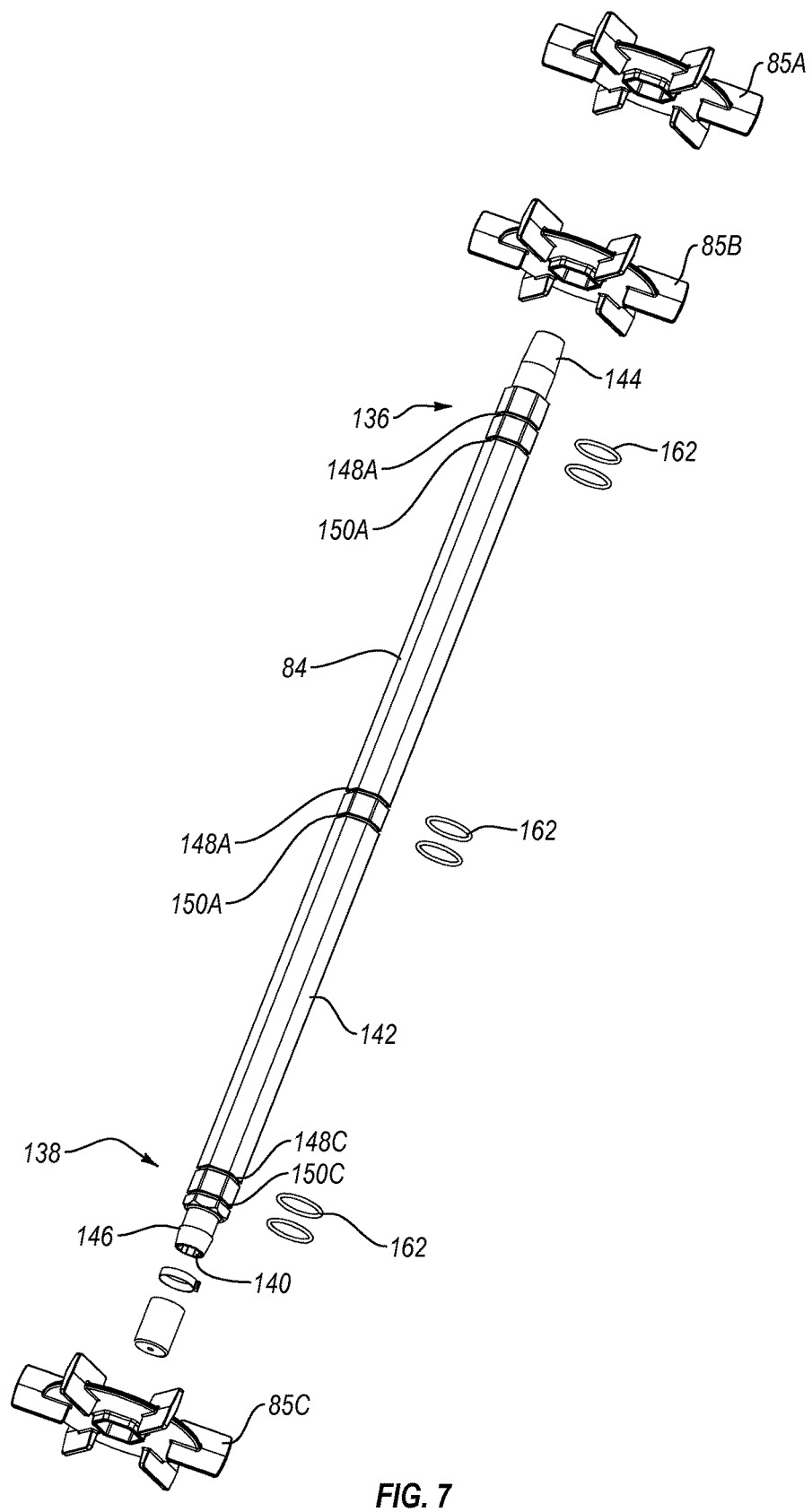
FIG. 7 is an exploded perspective view of the second tubular connector and impellers shown in FIG. 5.

As depicted in FIG. 7, formed at first end 136 is a tapered stem 144 that is configured to be received within second end 120 of first tubular connector 80 (FIG. 5) so as to form a secure, liquid tight seal therebetween. A barbed stem 146 is formed at second end 146. Exterior surface 84 extending between stems 144 and 146 has a transverse cross section that is polygonal, elliptical, or some other non-circular configuration. For example, the transverse cross section can be polygonal having 5, 6, 7 or more sides. Disposed at spaced apart locations along the length of exterior surface 142 are three pairs of annular grooves 148A-C and 150A-C that encircle second tubular connector 84.

Figure 8:
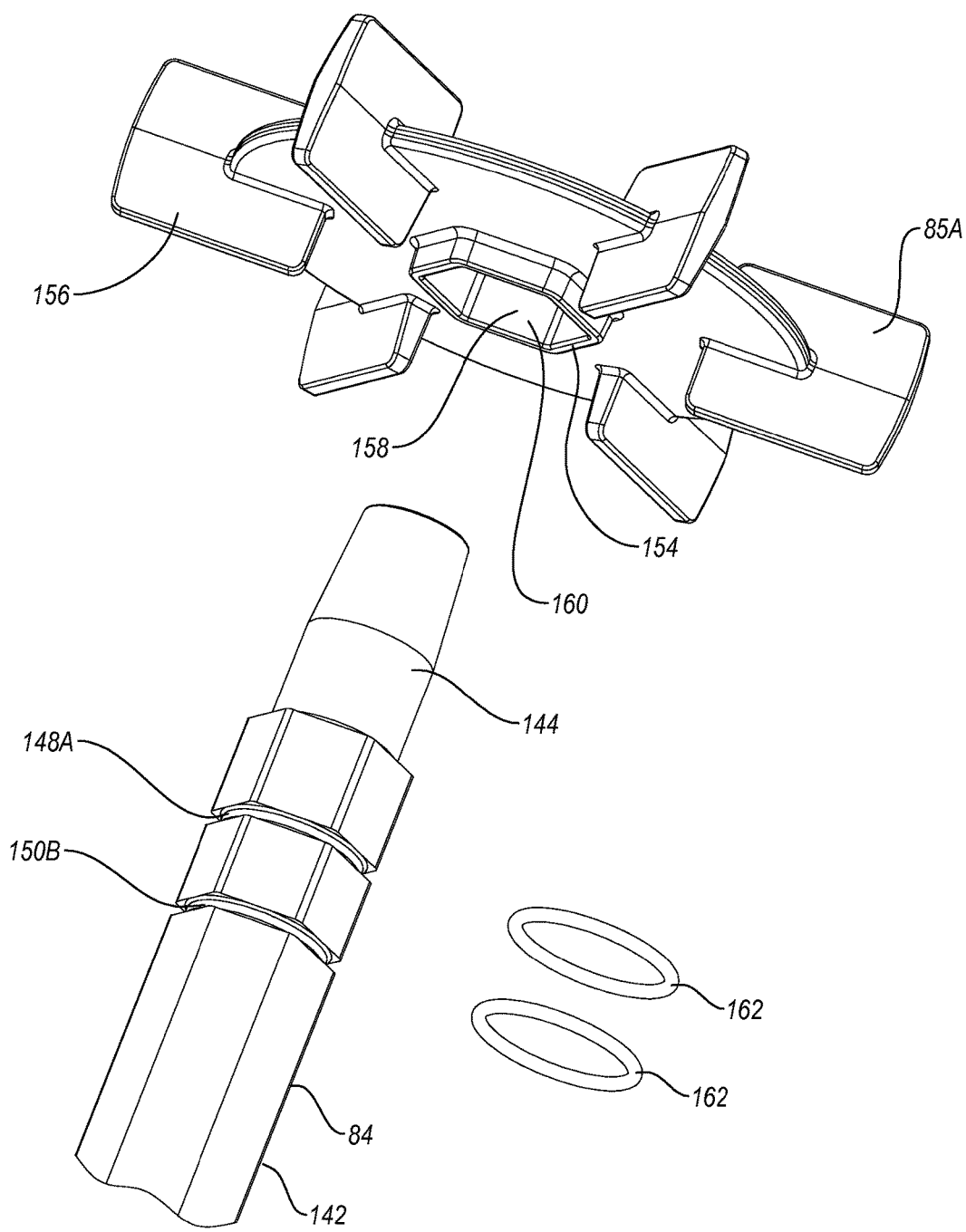
FIG. 8 is an enlarged exploded perspective view of the first end of the second tubular connector and an impeller to be received thereon.
Figure 9:
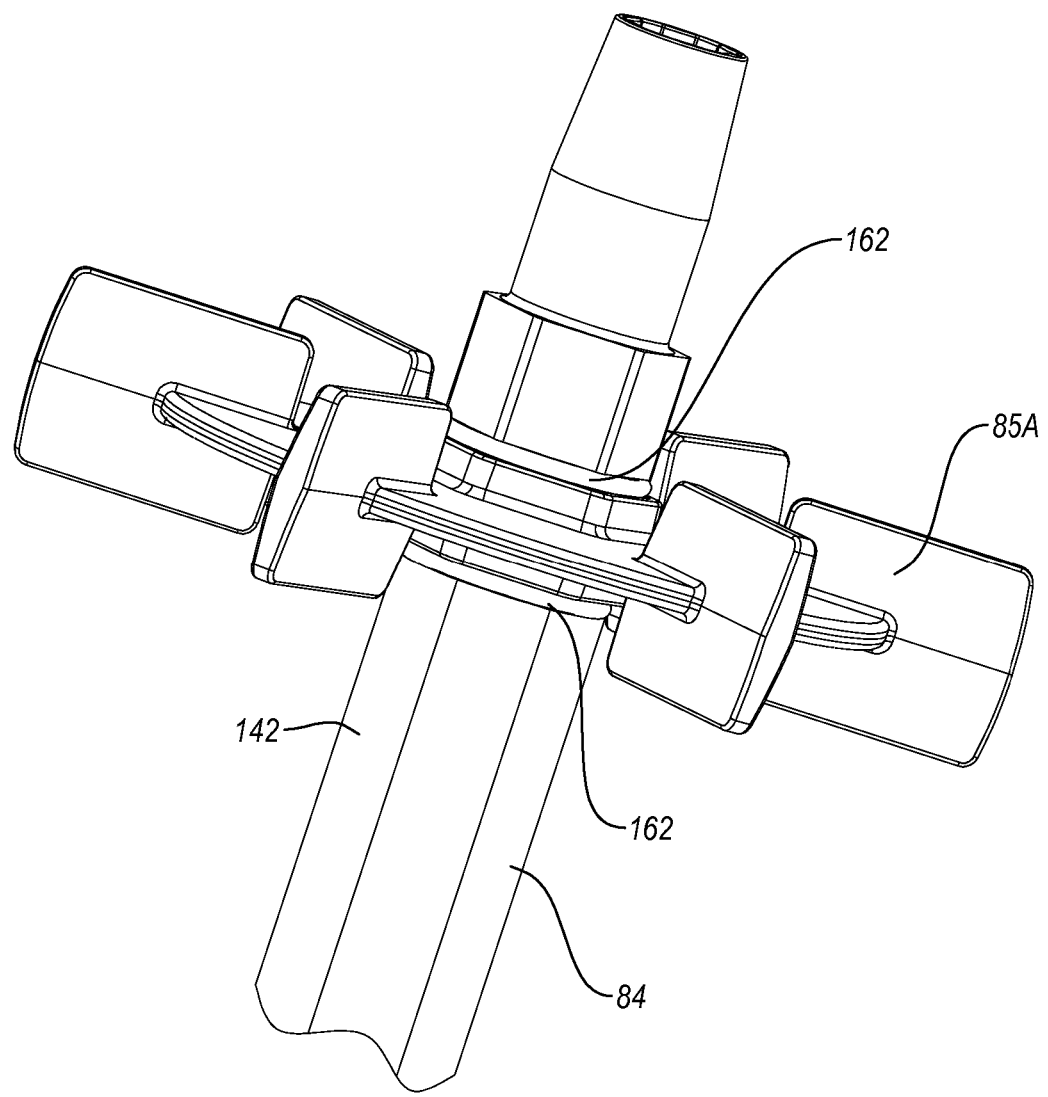
FIG. 9 is a perspective view of the components in FIG. 8 assembled.

Exterior surface 142 of second tubular connector 84 is configured to receive impellers 85A-C so that they can be fixed thereon. As used in the specification and appended claims, the term "impeller" is broadly intended to include all conventional types of impellers and impeller blades along with other structures that can be mounted on second tubular connector 84 so that when second tubular connector 84 is rotated within container 12, the structures can uniformly mix the fluid within container 12. In the current embodiment, as depicted in FIG. 8, each impeller 85 comprises a central hub 154 having a plurality of fins 156 outwardly projecting therefrom. Again, fins 156 can comprise any type of impeller blade that will function for mixing in the intended application. Hub 154 has an interior surface 158 that bounds an opening 160 extending therethrough. Interior surface 158 has a configuration complementary to exterior surface 142 of second tubular connector 84 or is otherwise configured to engage exterior surface 142 so that when second tubular connector 84 is advanced through opening 160 of impeller 85, impeller 85 is keyed with or otherwise secured to second tubular connector 84 so that rotation of second tubular connector 84 along the longitudinal axis thereof causes impellers 85 to concurrently rotate therewith.

During assembly, each impeller 85A-C is slid along second tubular connector 84 until hub 154 is centrally located between a pair of corresponding grooves 148 and 150. Retainers 162 are received within grooves 148 and 150 to retain impellers 85 at the desired locations along second tubular connector 84. In one embodiment, retainers 162 comprise O-rings that are made from an elastomeric material such as silicone. Other materials can also be used. The O-rings are configured so that when they are received within annular grooves 148/150, the O-rings still radially outwardly project beyond exterior surface 142 of second tubular connector 84. Thus, the O-rings can be slid onto second tubular connector 84 on opposing sides of each impeller 85 so that when the O-rings are received within annular grooves 148/150 with impeller 85 disposed therebetween, the O-rings preclude impeller from sliding along the length of second tubular connector 84 past the O-rings. This configuration provides a simple way to manufacture and assemble second tubular connector 84 with impellers thereon and eliminates complex molding procedures and mechanical fasteners, such as set screws, which can become loose or can form small holes or crevices into which cells or microorganisms can stagnate and die. The configuration also eliminates the required use of adhesives which can potentially leach into and contaminate a culture.

In alternative embodiments, it is appreciated that other retainers 162 can also be used. For example, snap rings or clips, such as those having a C-shaped configuration, could be received within grooves 148/150 to secure impellers 85. In still other embodiments, it is appreciated that other conventional techniques, such as those discussed above, could be used to either permanently or removably secure impellers 85 to second tubular connector 84. Furthermore, in other alternative embodiments it is appreciated that not all of exterior surface 142 of second tubular connector 84 needs to be complementary to interior surface 158 of impellers 85. Rather, only the portion of exterior surface 142 between grooves 148 and 150 needs to have the complementary or otherwise engaging surface so as to mate with impellers 85.

Figure 10:
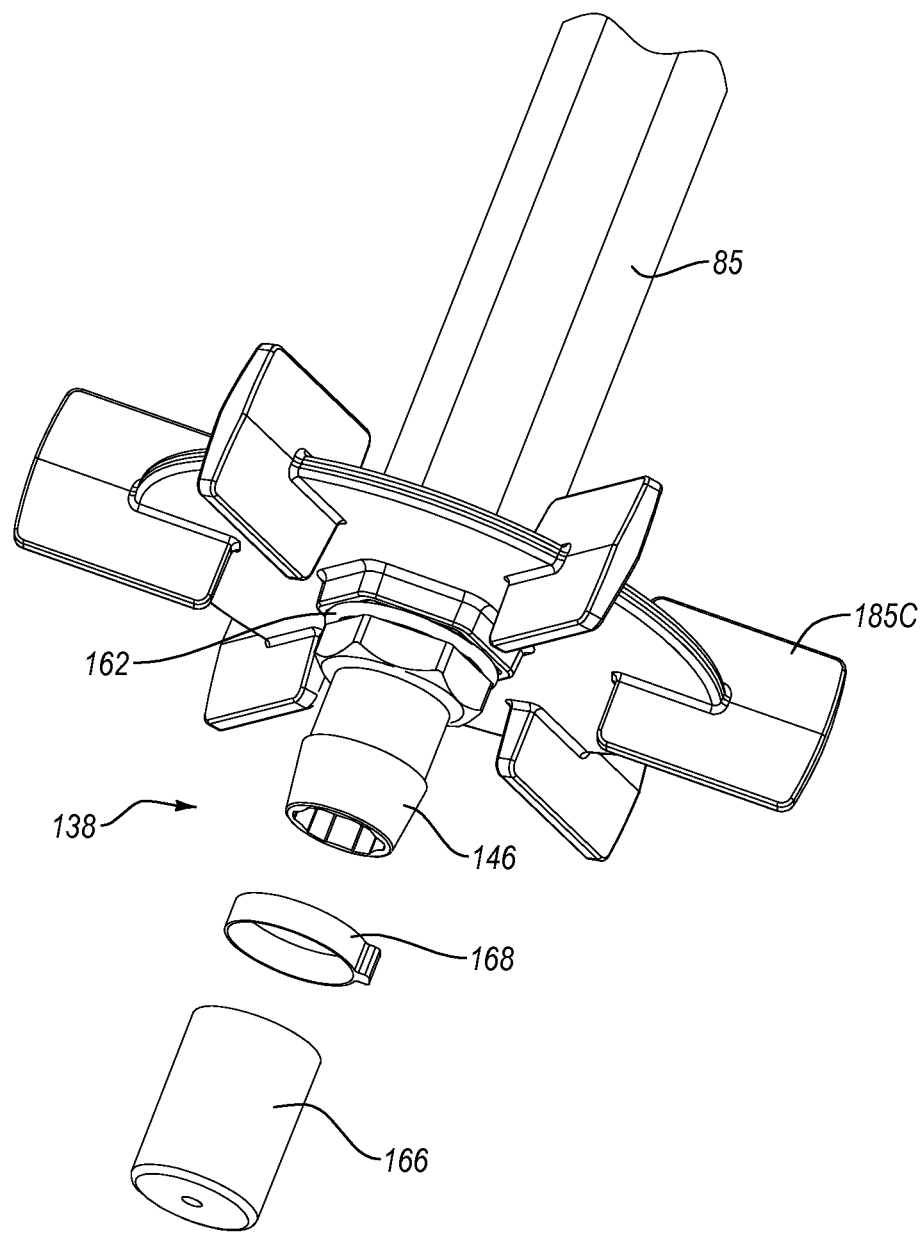
FIG. 10 is an enlarged exploded perspective view of the second end of the second tubular connector and an end cap to be received thereon.

Turning to FIG. 10, an end cap 166, such as made from a polymeric or elastomeric material, can be slid over stem 146 and secured by a fastener 168, such as a pull tie or crimp, so as to from a liquid tight seal at second end 138 of second tubular connector 84.

Figure 11:
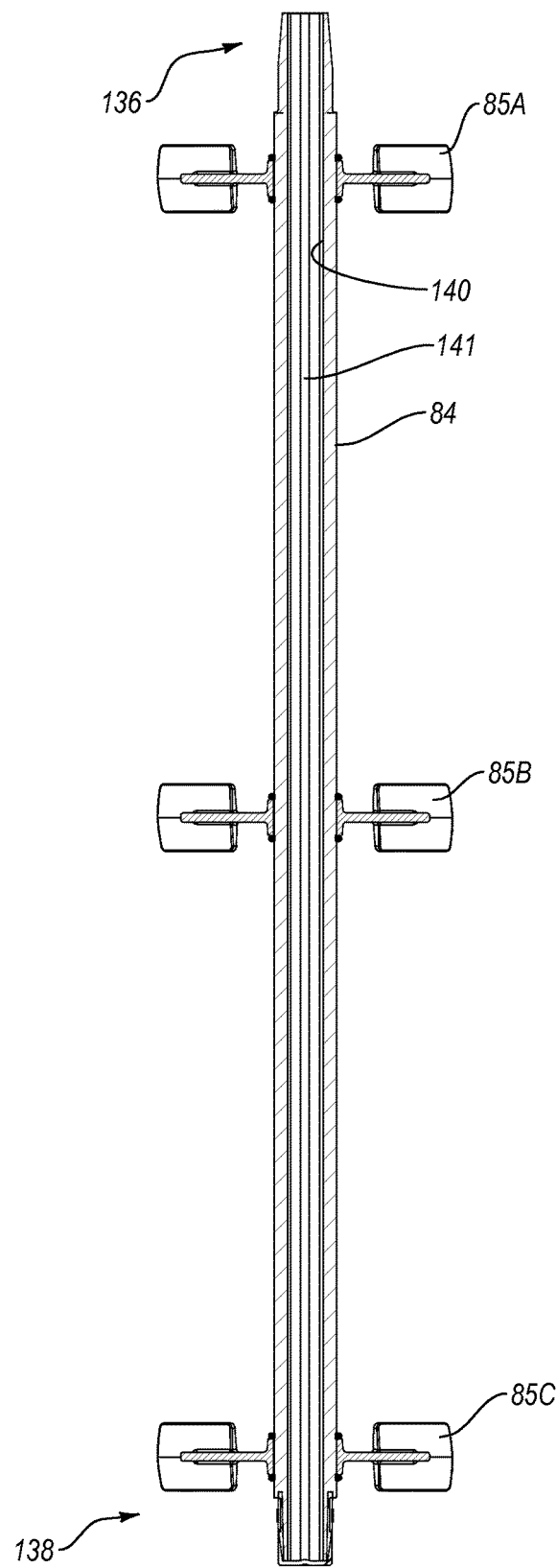
FIG. 11 is a cross sectional side view of the second tubular connector with the impellers thereon.

Turning to FIG. 11, interior surface 140 of second tubular connector 84 along the length thereof has a configuration that is complementary to the transverse cross section of second driver portion 114 on drive shaft 72 (FIG. 5) or is otherwise configured to engage second driver portion 114 so that when second driver portion 114 is received within passage 141 of second tubular connector 84, rotation of drive shaft 72 facilitates concurrent rotation of second tubular connector 84. For example, interior surface 140 of second tubular connector 84 and second driver portion 114 on drive shaft 72 can have complementary polygonal or other non-circular configurations.

It is appreciated that second driver portion 114 need not engage the full length of second tubular connector 84. However, because drive shaft 72 is typically stronger than second tubular connector 84, the more length of drive shaft 72 that directly engages along the length of second tubular connector 84, the more strength is imparted to second tubular connector 84. Thus, in general, in situations where greater torque will be applied to second tubular connector 84, more length of second driver portion 114 should engage second tubular connector 84. For example, second driver portion 114 can be configured to engage at least 20% and more commonly at least 40% or 60% of the total length of second tubular connector 84. Other percentages can also be used.

During assembly, impeller assembly 78 is coupled with container 12 as discussed above. The assembly can then be sterilized, such as by radiation, so that compartment 50 and the components therein are sterile. To facilitate shipping and storage, container 12 can be folded over at any location along the length of flexible first tubular connector 80 so as to minimize the length and size of the container assembly. During use, container 12 with impeller assembly 78 secured thereto is positioned within chamber 30 of support housing 14. Rotational assembly 82 is then removably connected to bottom surface 64 of housing 60 of drive motor assembly 59 so that hub 88 is aligned with motor mount 68. First end 100 of drive shaft 72 is advanced down through motor mount 68, through hub 86 of rotational assembly 82, through first tubular connector 80 and finally into second tubular connector 84.

In this position, drive shaft 72 is locked to motor mount 68 with first diver portion 112 engaging hub 88 and second driver portion 114 engaging second tubular connector 84, as discussed above. As a result, rotation of motor mount 68 by motor 70 facilitates rotation of drive shaft 72 which in turn facilitates the concurrent rotation of hub 88, first tubular connector 80, second tubular connector 84, and impellers 85 mounted on second tubular connector 84. In turn, rotation of impeller 85 facilities mixing and suspension of the fluid within compartment 50 of container 12. Further disclosure with regard to drive motor assembly 59, rotational assembly 82, and drive shaft 72 and how these elements operate and couple together, along with alternative embodiments thereof, is disclosed in United States Patent Publication Nos. 2011-0188928 A1, published Aug. 4, 2011; 2011-0310696, published Dec. 22, 2011 and 2006-0280028, published Dec. 14, 2006 which are incorporated herein by specific reference.

Embodiments of the inventive system have a number of advantages. For example, by using second tubular connector 84 which is rigid, a plurality of impellers can be mounted thereon which significantly increases the ability to mix the fluid within container 12. This is significantly helpful in situations such as where the fluid processing system is functioning as a fermentor for growing microorganisms. This is because fermentors typically require aggressive mixing to achieve and maintain the needed gas-liquid mass transfer with the fluid to keep the microorganisms alive and thriving. The system is also advantageous in that the container assembly is easy to manufacture, scalable, and disposable after use so the no cleaning or sterilization is required. As discussed above, by using first tubular connector 80 which is flexible, the container assembly can still be folded into a relatively small volume, thereby making it easier to sterilize, ship, and store. Furthermore, the system provides an easy, modular system for attaching impellers to second tubular connector 84. For example, different systems having different numbers of impellers can be designed using the same second tubular connector 84. In addition, because all of the impellers can be mounted on second tubular connector 84, only one separate connection to first tubular connector 80 is required, thereby simplifying assembly and minimizing locations for potential contamination. Other advantages also exist.

It is appreciated that the inventive system also has a number of alternative embodiments. For example, although second tubular connector 84 is shown having three impellers 85 mounted thereon, in other embodiments second tubular connector 84 can have 1, 2, 4, 5 or more impellers 85 mounted along the length thereof. It is also appreciated that the relative lengths of first tubular connector 80 and second tubular connector 84 can be varied. For example, in some embodiments, the length of second tubular connector 84 is at least 20%, 40% or 60% of the combined total length of first tubular connector 80 and second tubular connector 84. In other embodiments, the length of first tubular connector 80 is at least 20%, 40% or 60% of the combined total length of first tubular connector 80 and second tubular connector 84.

Figure 12:
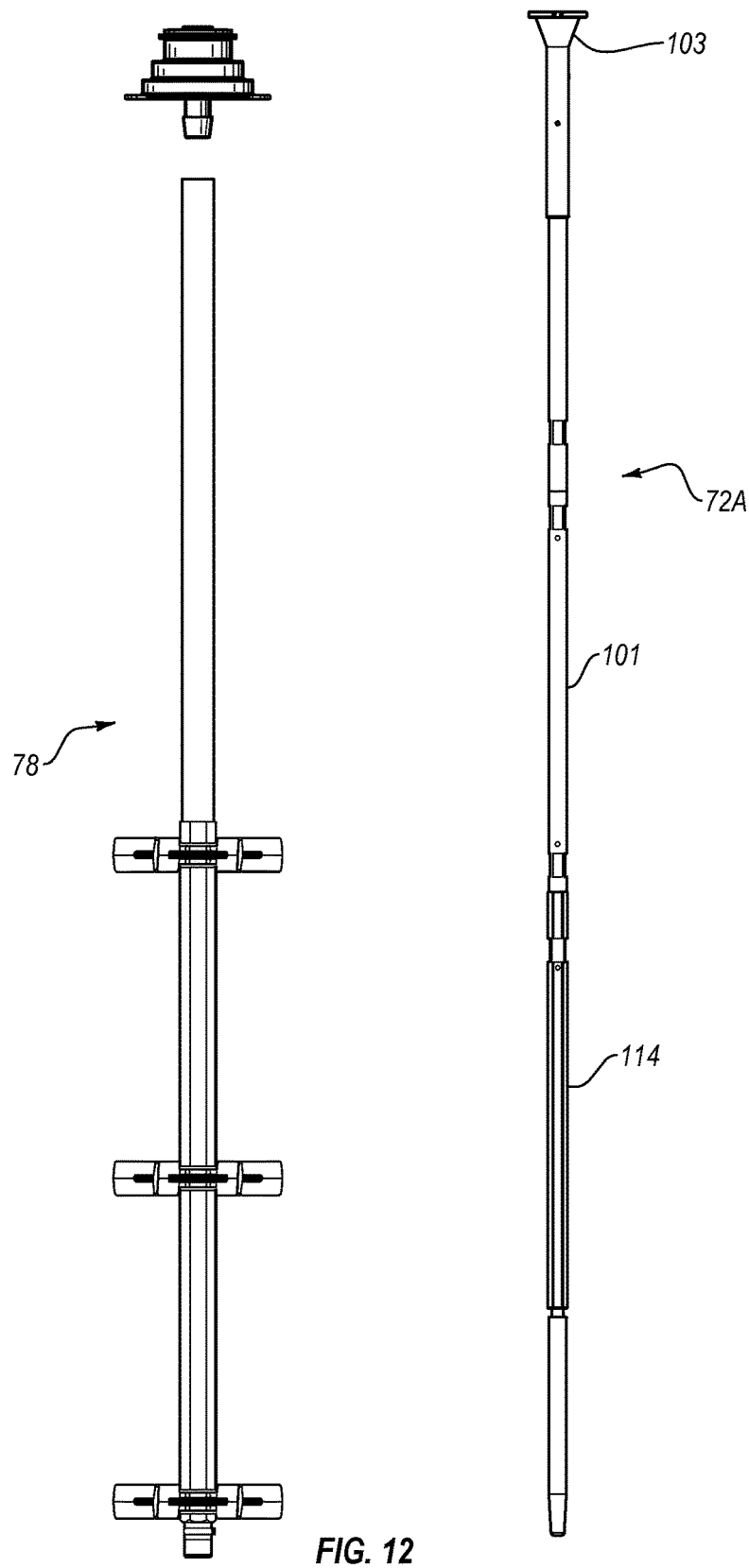
FIG. 12 is an elevated side view of an alternative embodiment of a drive shaft.

Depicted in FIG. 12 is an alternative embodiment of a drive shaft 72A. Like features between drive shaft 72 and 72A are identified by like reference characters. Drive shaft 72A is substantially identical to drive shaft 72 except that first driver portion 112 (FIG. 5) has been eliminated. As such, drive shaft 72 does not directly engage hub 88. However, hub 88 can still rotate by torque produced by first tubular connector 80.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A fluid mixing system comprising:
    a flexible bag having an interior surface bounding a compartment;
    an elongated first tubular connector disposed within the compartment of the flexible bag, the first tubular connector having a first end and an opposing second end, the first end of the first tubular connector being coupled with the flexible bag;
    an elongated second tubular connector disposed within the compartment of the flexible bag, the second tubular connector being more rigid than the first tubular connector and having a first end coupled to the second end of the first tubular connector;
    a drive shaft removably received within the first tubular connector and engaging the second tubular connector such that rotation of the drive shaft facilitates rotation of the second tubular connector; and a plurality of impellers being disposed on the elongated second tubular connector at spaced apart locations.

2. The fluid mixing system as recited in claim 1, wherein the drive shaft is removably received within the second tubular connector.

3. The fluid mixing system as recited in claim 1, further comprising a rotational assembly which includes a casing mounted to the flexible bag and a hub rotatably mounted to the casing, the hub having a passageway extending therethrough, the first end of the first tubular connector being secured to the hub.

4. The fluid mixing system as recited in claim 3, wherein the drive shaft engages the hub such that rotation of the drive shaft facilitates rotation of the hub.

5. The fluid mixing system as recited in claim 3, wherein rotation of the drive shaft facilitates concurrent rotation of the hub, first tubular connector, and second tubular connector.

6. The fluid mixing system as recited in claim 1, wherein the first tubular connector is sufficiently flexible that it can be bent along its length over an angle of 180° without plastic deformation and the second tubular connector is sufficiently rigid that it cannot be bent along its length over an angle of 40° without plastic deformation.

7. The fluid mixing system as recited in claim 1, wherein the plurality of impellers comprises at least three impellers.

8. The fluid mixing system as recited in claim 1, wherein the second tubular connector has a length that is at least 40% of the combined length of the first tubular connector and the second tubular connector.

9. The fluid mixing system as recited in claim 1, wherein the drive shaft directly engages an interior surface of the second tubular connector over at least 40% of the length of the second tubular connector.

10. The fluid mixing system as recited in claim 1, wherein the drive shaft is linear.

11. The fluid mixing system as recited in claim 1, wherein the first tubular connector is comprised of an elastomeric material and the second tubular connector is not comprised of an elastomeric material.

12. A fluid mixing system comprising:
a flexible bag having an interior surface bounding a compartment;
an elongated first tubular connector disposed within the compartment of the flexible bag, the first tubular connector having a first end and an opposing second end, the first end of the first tubular connector being coupled with the flexible bag;
an elongated second tubular connector disposed within the compartment of the flexible bag, the second tubular connector being more rigid than the first tubular connector and having a first end coupled to the second end of the first tubular connector, a first portion of the second tubular connector having an exterior surface with a transverse cross section that is non-circular; and
an impeller comprising a hub with an opening extending centrally therethrough and a plurality of fins outwardly projecting therefrom, the first portion of the second tubular connector being slidably received within the opening of the impeller and engaging the impeller such that rotation of the second tubular connector rotates the impeller.

13. The fluid mixing system as recited in claim 12, further comprising:
an annular groove encircling the second tubular connector on each opposing side of the impeller; and
a retainer received within each annular groove so as to radially outwardly project beyond the exterior surface of the second tubular connector.

14. The fluid mixing system as recited in claim 13, wherein each retainer comprises an elastomeric O-ring.

15. The fluid mixing system as recited in claim 12, wherein the transverse cross section of the first portion of the second tubular connector is polygonal.

16. The fluid mixing system as recited in claim 15, wherein the opening of the hub of the impeller has a polygonal configuration complementary to the first portion of the second tubular connector.

17. The fluid mixing system as recited in claim 12, wherein the first tubular connector is comprised of an elastomeric material and the second tubular connector is not comprised of an elastomeric material.

18. The fluid mixing system as recited in claim 12, further comprising a drive shaft removably received within the first tubular connector and engaging the second tubular connector.

19. A fluid mixing system comprising:
a flexible bag having an interior surface bounding a compartment;
an elongated first tubular connector disposed within the compartment of the flexible bag, the first tubular connector having a first end and an opposing second end, the first end of the first tubular connector being coupled with the flexible bag;
an elongated second tubular connector disposed within the compartment of the flexible bag, the second tubular connector being more rigid than the first tubular connector and having a first end coupled to the second end of the first tubular connector, a first portion of the second tubular connector having an exterior surface with a transverse cross section that is non-circular;
an impeller comprising a hub with an opening extending therethrough and a plurality of fins outwardly projecting therefrom, the first portion of the second tubular connector being slidably received within the opening of the impeller and engaging the impeller such that rotation of the second tubular connector rotates the impeller;
an annular groove encircling the second tubular connector on each opposing side of the impeller; and
a retainer received within each annular groove so as to radially outwardly project beyond the exterior surface of the second tubular connector.

20. The fluid mixing system as recited in claim 19, wherein each retainer comprises an elastomeric O-ring.

* * * * *